US010692226B2

(12) United States Patent
Bresch et al.

(10) Patent No.: US 10,692,226 B2
(45) Date of Patent: Jun. 23, 2020

(54) MEDICAL ATLAS REGISTRATION (71) Applicant: KONINKLIJKE PHILIPS N.V., Eindhoven (NL)

(72) Inventors: Erik Bresch, Eindhoven (NL); Vlado Menkovski, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/097,653

(22) PCT Filed: May 4, 2017

(86) PCT No.: PCT/EP2017/060634
§ 371 (c)(1),
(2) Date: Oct. 30, 2018

(87) PCT Pub. No.: WO2017/191248
PCT Pub. Date: Nov. 9, 2017

(65) Prior Publication Data
US 2019/0139237 A1 May 9, 2019

(30) Foreign Application Priority Data

May 4, 2016 (EP) .................................. 16168226

(51) Int. Cl.
*G06T 7/33* (2017.01)
*G16H 30/40* (2018.01)
*G06T 7/00* (2017.01)
(52) U.S. Cl.
CPC .............. *G06T 7/33* (2017.01); *G06T 7/0012* (2013.01); *G16H 30/40* (2018.01);
(Continued)

(58) Field of Classification Search
CPC ..................... G06T 7/33; G06T 7/0012; G06T 2207/20016; G06T 2207/20081;
(Continued)

(56) References Cited

U.S. PATENT DOCUMENTS 10,032,281 B1 * 7/2018 Ghesu ....................... G06T 7/12
2007/0036402 A1 2/2007 Cahill et al.
(Continued)

OTHER PUBLICATIONS

Gonzalez, A., "Segmentation of Brain MRI Structures with Deep Machine Learning", Master in Artificial Intelligence (UPC-URV-UB), Master of Science Thesis, Jun. 22, 2012, 56 pages.
(Continued)

*Primary Examiner* — Pinalben Patel (57) ABSTRACT

A system and method are provided for enabling atlas registration in medical imaging, said atlas registration comprising matching a medical atlas 300, 302 to a medical image 320. The system and method may execute a Reinforcement Learning (RL) algorithm to learn a model for matching the medical atlas to the medical image, wherein said learning is on the basis of a reward function quantifying a degree of match between the medical atlas and the medical image. The state space of the RL algorithm may be determined on the basis of a set of features extracted from i) the atlas data and ii) the image data. As such, a model is obtained for medical atlas registration without the use, or with a reduced use, of heuristics. By using a machine learning based approach, the solution can easily be applied to different atlas matching problems, e.g., to different types of medical atlases and/or medical images.

12 Claims, 5 Drawing Sheets (52) U.S. Cl.
CPC ............... *G06T 2207/20016* (2013.01); *G06T 2207/20081* (2013.01); *G06T 2207/20084* (2013.01); *G06T 2207/20128* (2013.01)

(58) Field of Classification Search
CPC ........... G06T 2207/20084; G06T 2207/20128; G16H 30/40
See application file for complete search history.

(56) References Cited

U.S. PATENT DOCUMENTS

| | | | | |
|---|---|---|---|---|
| 2010/0266170 | A1* | 10/2010 | Khamene | G06K 9/469 382/128 |
| 2010/0272330 | A1 | 10/2010 | Pekar et al. | |
| 2011/0216954 | A1 | 9/2011 | Sundar et al. | |
| 2015/0356367 | A1 | 12/2015 | Han | |
| 2016/0163035 | A1* | 6/2016 | Chang | G06K 9/4628 382/149 |
| 2017/0116497 | A1* | 4/2017 | Georgescu | A61B 6/032 |
| 2019/0340743 | A1* | 11/2019 | Ranson | G06T 7/0002 |
| 2019/0346272 | A1* | 11/2019 | Banino | G01C 21/20 |

OTHER PUBLICATIONS

Lofti, et al., "Improving probabilistic image registration via reinforcement learning and uncertainty evaluation", Sep. 22, 2013 (Sep. 22, 2013), Network and Parallel Computing; [Lecture Notes in Computer Science; Lect.Notes Computer],Springer International Publishing, CHAM, pp. 187-194.

Mahyari, T., "Uncertainty in Probabilistic Image Registration", Master Thesis, Jun. 3, 2013, Simon Fraser University, Burnaby, BC,Canada, ISBN: 978-0-499-23962-4, Retrieved from the Internet: URL:http ://summit.sfu.ca/system/files/iritemsl/12981/etd7863JLotfiMahyari.pdf, 73 pages.

Brebisson, et al., "Deep Neural Networks for Anatomical Brain Segmentation", 2015 IEEE Conference on Computer Vision and Pattern Recognition Workshops (CVPRW), IEEE, Jun. 7, 2015, pp. 20-28.

Vaidhya, et al., "Multi-modal Brain Tumor Segmentation Using Stacked Denoising Autoencoders", Oct. 5, 2015, Network and Parallel Computing; [Lecture Notes in Computer Sc ience; Lect. Notes Computer], Springer International Publishing, CHAM, pp. 181-194.

Volodymyr, "Human-level control through deep reinforcement learning", Feb. 26, 2015, vol. 518, Nature, pp. 529-533.

Harmon, et al., "Reinforcement Learning: A Tutorial", Jan. 1, 1996, XP055314587, Retrieved from the Internet: URL:http://www.cs.toronto.edu/*zemel/documents/411/rltutorial.pdf [retrieved on Oct. 27, 2016].

Bresch, et al., "Region Segmentation in the Frequency Domain Applied to Upper Airway Real-Time Magnetic Resonance Images", IEEE Transactions on Medical Imaging, vol. 28, No. 3, Mar. 2009, pp. 323-338.

* cited by examiner

MEDICAL ATLAS REGISTRATION

This application is the U.S. National Phase application under 35 U.S.C. § 371 of International Application No. PCT/EP2017/060634, filed on May 4, 2017, which claims the benefit of European Application Serial No. 16168226.5 filed May 4, 2016. These applications are hereby incorporated by reference herein.

FIELD OF THE INVENTION

The invention relates to a system and a method for enabling atlas registration in medical imaging. The invention further relates to a workstation comprising the system. The invention further relates to a computer readable medium comprising instructions for causing a processor system to perform the method.

BACKGROUND OF THE INVENTION

It is known to provide a graphical annotation or segmentation of a medical image of a patient by registering a medical atlas with the medical image. For example, a medical atlas may comprise a geometrical description of organs, e.g., of their bounding contours, for a particular field of view (FOV). However, medical images can vary significantly across patients due to patients having organs of different shapes and sizes. As such, registering a medical atlas to a medical image is considered a non-trivial task.

Mathematically, medical atlas registration may be described as an optimization problem, where a set of parameter values of a model need to be determined that define a transformation, or set of transformations, of the medical atlas that provides the best registration to the medical image according to a match function. It has been recognized that one of the core challenges in such medical atlas registration comes from the fact that for most match functions, only perfect alignment between the medical atlas and the medical image produces a perfect match. Incremental improvements may be misleading. Namely, the optimization problem is generally not convex. As such, gradient descent optimizers are likely to get "trapped" in a local minimum. At the same time, evaluating all possible (sequences of individual) transformations is not feasible as it is a mathematically intractable problem.

A possible solution to the above problem is described in the paper "*Region segmentation in the frequency domain applied to upper airway real-time magnetic resonance images*" by Erik Bresch et al., Medical Imaging, IEEE Transactions on 28.3 (2009): 323-338. Herein, a method of atlas registration for a midsagittal MRI scan of the human vocal tract is described which employs a hierarchy of restricted transformations of the atlas. Hereby, rough large scale alignments are carried out first until no match fit can be achieved, and only then a more fine-grained warping is carried out. In the paper, a series of four distinct, less and less restricted warping operations is employed. This temporary restriction of the transformation space is said to lead to a smoothing of the energy landscape of the optimization problem, which in turn alleviates the risk of getting "trapped" in a local minimum.

However, the solution proposed in the above paper is designed only for this particular atlas, with heuristic components that are only empirically justified. Applying similar approaches to different atlas matching problems is a slow and cumbersome task.

A master thesis titled "*Uncertainty in Probabilistic Image Registration*" by Tayebeh Lotfi Mahyari describes in section 3.5 using reinforcement learning to guide an iterative image registration procedure. Furthermore, a publication titled "*Improving Probabilistic Image Registration via Reinforcement Learning and Uncertainty Evaluation*" by Tayebeh Lofti et al. describes a framework for probabilistic image registration which involves assigning probability distributions over spatial transformations.

Technical background on deep neural networks may be obtained from "*Deep neural networks for anatomical brain segmentation*" by De Brebisson Alexandre et al, 7 Jun. 2015. Technical background on auto encoders may be obtained from "*Multi-modal Brain Tumor Segmentation Using Stacked Denoising Autoencoders*" by Vaidhya Kiran et al, 5 Oct. 2015. Technical background on (deep) reinforcement learning may be obtained from "*Human-level control through deep reinforcement learning*" in Nature, 26 Feb. 2015 and from the tutorial "*Reinforcement Learning: A Tutorial Scope of Tutorial*", 1 Jan. 1996.

SUMMARY OF THE INVENTION

It would be advantageous to have an improved system or method for generating a model for atlas registration in medical imaging.

A first aspect of the invention provides a system for enabling atlas registration in medical imaging, said atlas registration comprising matching a medical atlas to a medical image, the system comprising:

a first input interface for accessing atlas data defining the medical atlas;

a second input interface for accessing image data of the medical image;

a processor configured to:
  execute a Reinforcement Learning algorithm to learn a model for matching the medical atlas to the medical image, wherein said learning is on the basis of a reward function quantifying a degree of match between the medical atlas and the medical image;
  determine a state space for the Reinforcement Learning algorithm on the basis of a set of features extracted from i) the atlas data and ii) the image data. A further aspect of the invention provides a workstation comprising the system. A further aspect of the invention provides a computer readable medium comprising transitory or non-transitory data representing a model for atlas registration in medical imaging as generated by the system.

A further aspect of the invention provides a method of enabling atlas registration in medical imaging, said atlas registration comprising matching a medical atlas to a medical image, comprising:

accessing atlas data defining the medical atlas;

accessing image data of the medical image;

executing a Reinforcement Learning algorithm to learn a model for matching the medical atlas to the medical image, wherein said learning is on the basis of a reward function quantifying a degree of match between the medical atlas and the medical image; and determining a state space for the Reinforcement Learning algorithm on the basis of a set of features extracted from i) the atlas data and ii) the image data.

A further aspect of the invention provides a computer readable medium comprising transitory or non-transitory data representing instructions to cause a processor system to perform the method.

The above measures involve accessing image data of a medical image of a patient, as acquired by an imaging modality such as Computed Tomography (CT), Magnetic Resonance Imaging (MRI), Ultrasound (US), Positron Emission Tomography (PET), etc. Moreover, atlas data is accessed which defines a medical atlas. Such definition may be in a manner known per se in the art of medical atlas generation. For example, the atlas data may comprise a geometrical description of the bounding contours of organs. Another example is that the medical atlas may be a template image, with the atlas data being template image data.

A model for matching the medical atlas to the medical image is learned using a Reinforcement Learning (RL) algorithm. Reinforcement Learning algorithms are known per se in the art of machine learning and are known to make use of training model comprising a set of environment states defining a state space and a set of actions defining an action space. As output, a learned model is obtained, referring to a mathematical expression or algorithm, whose parameters have been learned during training and which is configured to compute the value of each possible action given a particular state of the system. Such actions may include transformation actions such as translations, rotations, deformations, etc., which may be restricted, e.g., in range, magnitude, distance, etc. After having been generated, the model may be queried, e.g., using an explore-exploit algorithm, for values of each transformation action given a particular state. For example, a highest value may represent a highest reward and thus a 'best' transformation action in accordance with a reward function.

The reward function used in the RL algorithm may quantify the degree to which the transformed medical atlas matches the medical image. For example, if the medical atlas is constituted by a template image, the reward function may be a sum of absolute differences (SAD) between pixel values of the medical image and the transformed medical atlas. In general, the reward function may be selected to match the type of medical atlas, e.g., whether the medical atlas is represented by image data and/or represented by geometric data.

The inventors have recognized that Reinforcement Learning may address the problem of medical atlas registration since RL is well suited for modelling so-termed delayed rewards. Namely, the co-existence in medical atlas registration of a global minimum next to one or more local minima may represent such delayed rewards, in that the reward (e.g., reaching the global minimum) may only be reached after a delay (e.g., a reduction in immediate reward when transitioning from a local minimum to the global minimum).

However, the inventors have further recognized that RL cannot be directly applied to the problem of medical atlas registration as the state space has a too high dimensionality for known RL algorithms. Namely, the state space would normally include the contents of the medical atlas and that of the medical images, e.g., all of its pixel values, which would yield a state space having a too large size and being unsuitable for RL.

In accordance with the above measures, the state space is determined based on higher level features instead of using the lower level atlas data or image data directly. Namely, a set of features is extracted from the atlas data and the image data. As such, features which are intended to be informative and non-redundant are extracted, e.g., using known feature extraction algorithms, thereby obtaining a reduced representation of the medical atlas and the image data. Such a reduced representation enables a state space with lower dimensionality. Effectively, a dimensionality reduction of the state space is obtained.

The above measures have the effect that a model is obtained for atlas registration in medical imaging without the use, or with a reduced use, of heuristics. Namely, by using a machine learning based approach, the solution can easily be applied to different atlas matching problems, e.g., to different types of medical atlases and/or medical images. In particular, the above measures enable the use of Reinforcement Learning as machine learning algorithm which is particularly well suited to the problem of atlas registration and which may be applied to the problem based on at least the state space having been suitably reduced.

In addition, the processor may be configured to determine an action space for the Reinforcement Learning algorithm on the basis of a predefined set of transformation actions which are available to be applied to the medical atlas. The Reinforcement Learning may be applied to atlas registration by providing transformations as actions. Here, the term 'transformation action' may refer to a transformation which constitutes a part of the overall transformation of the medical atlas to the medical image. For example, a transformation action may be associated with, and only apply to, a selected bounding contour. Another example is that one transformation action may define a translation of a selected bounding contour, whereas another transformation action may define a rotation of the selected bounding contour. By repeatedly querying the model and selecting transformation actions, a sequence of transformation actions may be obtained which, when applied to the medial atlas, deforms the medical atlas so as to match the medical image, thereby obtaining a registration of the medical atlas to the medical image. The action space for the Reinforcement Learning algorithm may be determined on the basis of a predefined set of transformation actions which are available to be applied to the medical atlas. For example the set of transformation actions may be part of the medical atlas definition. A specific example is that, in addition to the medical atlas defining a contour or a set of contours, a set of possible transformations of that contour or set of contours may be defined by the medical atlas and/or the atlas data.

The action space may be structured into different levels, wherein each of the different levels comprises a subset of the transformation actions, and wherein the different levels form a hierarchy of transformation actions in which selection of a sequence of transformation actions by the Reinforcement Learning algorithm is restricted to a downward progression in the hierarchy. Similarly to the state space, also the action space is likely to be too large to be directly applied to RL. The inventors have recognized that the hierarchical structuring of transformations as described in the aforementioned paper "*Region segmentation in the frequency domain applied to upper airway real-time magnetic resonance images*", herein incorporated by reference with respect to said hierarchical structuring as described in section IV.C "*Hierarchical Gradient Descent Procedure*", typically yields a reduction of the size of the action space, as the number of sequences of transformation actions may be reduced by each of the levels only comprising a subset of all available transformation actions. For example, the hierarchy may be from less restrictive transformation actions to more restrictive transformation actions. In a specific example, a highest hierarchy level may comprise only global or regional transformation actions whereas a following hierarchy level may comprise only local transformation actions. Here, the terms global, regional and local may refer to a decreasing spatial extent to which the transformation actions apply. For example, a global transformation action may apply to all bounding contours of a medical atlas, whereas a local transformation action may only apply to a selected bounding contour. In this example, in the accompanying action space, a local transformation action cannot be followed by a global transformation action. The effect of the above measures is that the set of transformation actions which is available at any point in time, e.g., in any state in the state space, is made manageable for the RL algorithm.

Optionally, the processor is configured to learn the set of features to be extracted from the atlas data and the image data using a machine learning algorithm. For example, the processor may be configured to apply a Convolutional Neural Network (CNN) or Autoencoder to the atlas data and the image data to determine the set of features. The CNN may be a Deep CNN. The Autoencoder may be a Deep Autoencoder. Deep Learning approaches such as said Deep CNN (which is similar to the DeepQ Network approach described in "Human-level control through deep reinforcement learning", Nature 518, 529-533, 26 Feb. 2015) and Deep Autoencoder algorithms have been found to be well suited for feature extraction from the atlas data and the image data. It is noted that for a Deep Autoencoder, the state space representation model (the Autoencoder) may be learned independently of the RL algorithm. If a Deep CNN is used directly to query the value of each action given a state, the training of the Deep CNN may be performed by the RL algorithm.

Optionally, the action space comprises one or more transition actions defining transitions between the different levels. By adding transition actions to one or more of the levels, the Reinforcement Learning agent of the RL algorithm may evaluate actions at a certain level, or switch to a different level to evaluate the actions of the different level. Optionally, the processor is configured to perform said hierarchically structuring of the action space using a machine learning algorithm or using pre-determined heuristics.

Optionally, the processor is configured to determine the state space for the Reinforcement Learning algorithm further based on a current level in the action space. The current level in the action space co-defines a current state in the state space. This may enable the RL algorithm to learn to transform the medical atlas in a hierarchical manner, e.g., starting from global transformations to local transformations. For example, a current-level variable may be 'attached' to the medical atlas concept in the case of deep CNN. In the case of a Deep Autoencoder, this variable may be attached to the state. In both cases, the value of the current-level variable may be used as input to the RL agent, which in turn may allow for limiting the number of transformation actions which are available in a current state.

Optionally, the processor is configured to determine the state space for the Reinforcement Learning algorithm further based on landmark data defining landmarks in the medical atlas. The medical atlas may be accompanied by landmark data defining landmarks in the medical atlas, referring to anatomical structures which may be used as points of orientation for locating other anatomical structures. Such landmarks may be used directly or indirectly as features to determine the state space of the Reinforcement Learning algorithm.

Optionally, the set of transformation actions which is available to be applied to the medical atlas is defined by the atlas data.

Optionally, the Reinforcement Learning algorithm is a Deep Reinforcement Learning algorithm.

It will be appreciated by those skilled in the art that two or more of the above-mentioned embodiments, implementations, and/or optional aspects of the invention may be combined in any way deemed useful.

Modifications and variations of the method and/or the computer program, which correspond to the described modifications and variations of the system, can be carried out by a person skilled in the art on the basis of the present description.

A person skilled in the art will appreciate that the system and method may be applied to multi-dimensional image data, e.g., to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the Figures, elements which correspond to elements already described may have the same reference numerals.

LIST OF REFERENCE NUMBERS

The following list of reference numbers is provided for facilitating the interpretation of the drawings and shall not be construed as limiting the claims.
020 atlas data repository
022 atlas data defining medical atlas
040 image data repository
042 image data of medical image
062 model data representing model
100 system for enabling atlas registration
120 first input interface
140 second input interface 160 processor
200 method for enabling atlas registration
210 accessing atlas data
220 accessing image data
230 determining state space
240 determining action space
250 executing RL algorithm
260 computer readable medium
270 instructions stored as non-transient data
300 (unregistered) medical atlas
302 registered medical atlas
310 image model of medical atlas
320 medical image

DETAILED DESCRIPTION OF EMBODIMENTS

Figure 1:
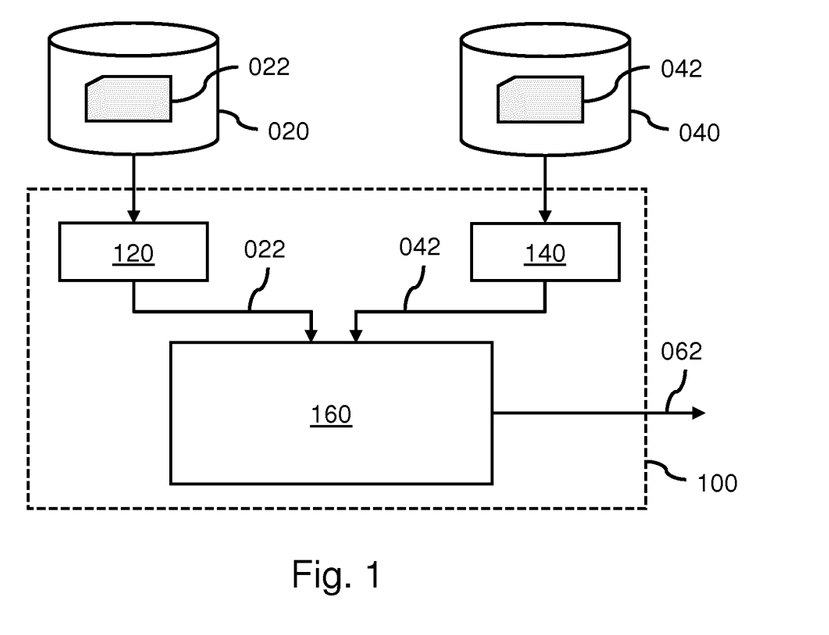
FIG. 1 shows a system for enabling atlas registration in medical imaging.

FIG. 1 shows a system 100 for enabling atlas registration in medical imaging. The system 100 is shown to comprise a first input interface 120 for accessing atlas data 022 defining a medical atlas, and a second input interface 140 for accessing image data 042 of a medical image. In the example of FIG. 1, both types of data are shown to be accessed from separate repositories, namely an atlas data repository 020 and an image data repository 040. For example, the atlas data repository 020 and/or the image repository 040 may be constituted by, or be part of, a Picture Archiving and Communication System (PACS) of a Hospital Information System (HIS) to which the system 100 may be connected or comprised in. Accordingly, the system 100 may obtain access to the atlas data 020 and/or the image data 040 via the HIS. Alternatively, the atlas data 020 and/or the image data 040 may be accessed from an internal data storage of the system 100. In general, each or both types of input interfaces 120, 140 may take various forms, such as a network interface to a local or wide area network, e.g., the Internet, a storage interface to an internal or external data storage, etc.

The system 100 is further shown to comprise a processor 160 which is connected to the respective input interfaces 120, 140 to obtain access to the atlas data 020 and the image data 040. The processor 160 is configured to, during operation of the system 100, execute a Reinforcement Learning algorithm to learn a model for matching the medical atlas to the medical image, wherein said learning is on the basis of a reward function quantifying a degree of match between the medical atlas and the medical image. Moreover, before or as part of said execution, the processor 160 may determine a state space for the Reinforcement Learning algorithm on the basis of a set of features extracted from i) the atlas data and ii) the image data, and determine an action space for the Reinforcement Learning algorithm on the basis of a set of transformation actions available to be applied to the medical atlas. As such, the Reinforcement Learning algorithm may be executed on the basis of the determined state space and action space. As output, the processor 160 may produce model data 062 representing the learned model. Although not shown explicitly in FIG. 1, the model data 062 may be stored, e.g., in a database, used by the system 100 to perform atlas registration, be provided to another system or apparatus to perform atlas registration, etc.

It is noted that various operations of the system 100, including various optional aspects thereof, will be further explained with reference to FIGS. 2A-4.

The system 100 may be embodied as, or in, a single device or apparatus, such as a personal computer, workstation, server or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the first input interface, the second input interface and the processor, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2A:
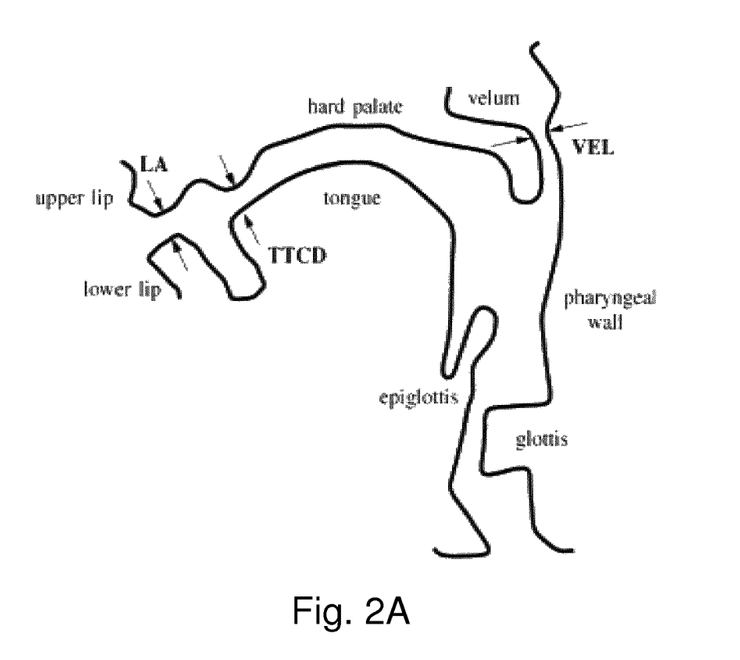
FIG. 2A shows anatomical structures in the human vocal tract.

FIG. 2A shows anatomical structures in the human vocal tract, which is used in this and the following figures as an example of an application area of atlas registration. In particular, FIG. 2A shows a selection of anatomical organs in the midsagittal view of the human vocal tract, including the tongue, hard palate, (epi)glottis and pharyngeal wall.

Figure 2B:
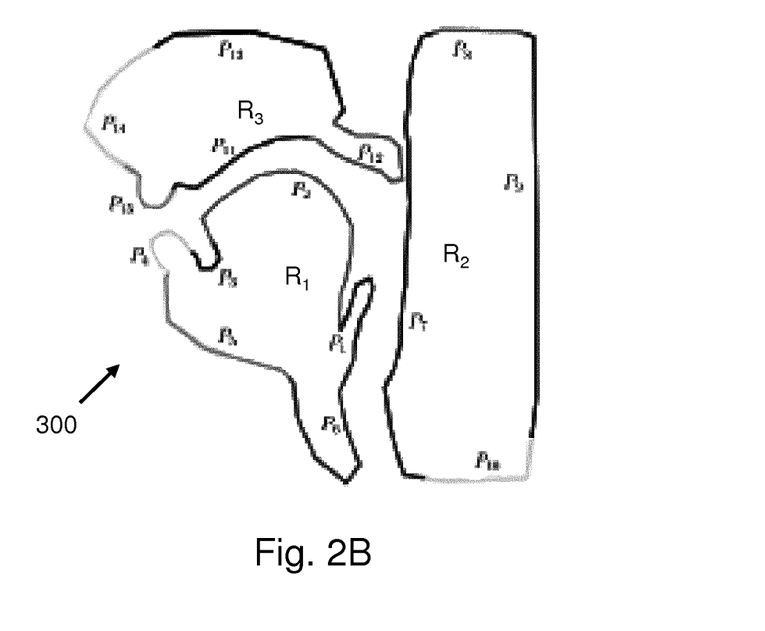
FIG. 2B shows a medical atlas for the human vocal tract.

FIG. 2B shows a medical atlas 300 for the human vocal tract. In this example, the atlas comprises a geometrical description of the anatomical organs in the midsagittal view of the human vocal tract, in that the atlas data defines the bounding contours of the anatomical organs. In particular, the atlas 300 is shown to comprise the boundaries of three distinct regions of interest $R_1$, $R_2$, $R_3$. Moreover, various landmarks have been defined along the bounding contours, e.g., in the form of landmark data, as also indicated by $P_x$ in FIG. 2B.

Figure 2C:
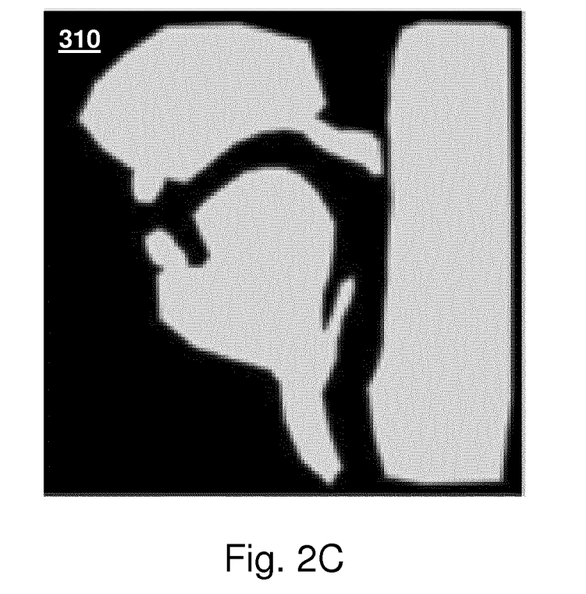
FIG. 2C shows an image model of the medical atlas.

FIG. 2C shows an image model 310 of the medical atlas, which may optionally accompany a geometric description of a medical atlas and which may relate the topological information of FIG. 2B to the generally expected intensity image that would arise from, in this example, an MRI scan. The image model 310 is shown to be idealized to have three equal intensity regions representing tissue, against a black background representing air.

Figure 3A:
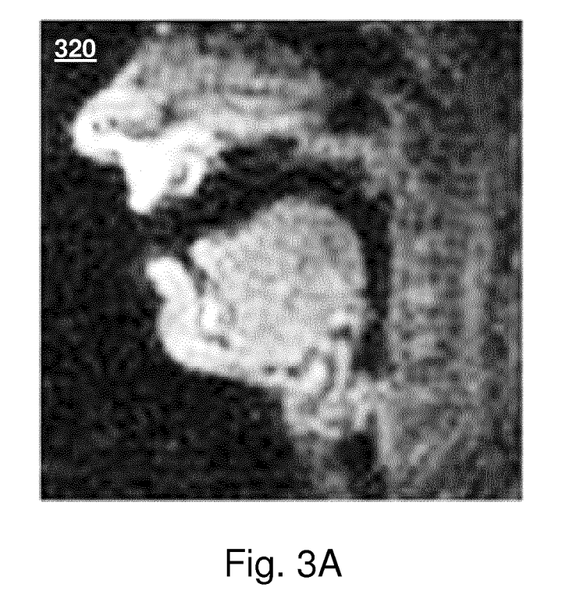
FIG. 3A shows a medical image of the human vocal tract of a patient.
Figure 3B:
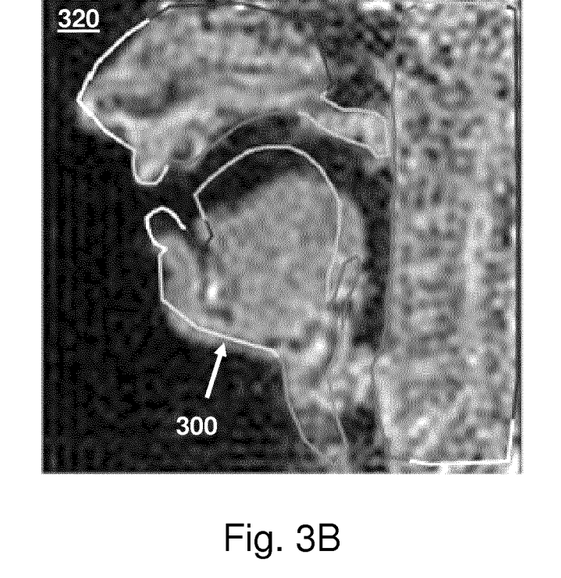
FIG. 3B shows the medical atlas overlaying the medical image, with the medical atlas not, or only globally, having been registered to the medical image.

FIG. 3A shows a medical image 320 of the human vocal tract of a patient. This medical image 320 provides approximately the same field of view (FOV) of the human vocal tract as the medical atlas 300 of FIG. 2B, and consequently shows the same general structure of anatomical organs. However, the exact shape and position of the anatomical organs differs in detail from the representation by the medical atlas. Consequently, it is not possible to simply apply the medical atlas to the medical image 320. Namely, the result of such application is shown in FIG. 3B, where it can be seen that the bounding contours of the medical atlas 300 mismatch the actual contours of anatomical organs shown in the medical image 320. It is noted that global registration will also not yield the desired match.

Figure 3C:
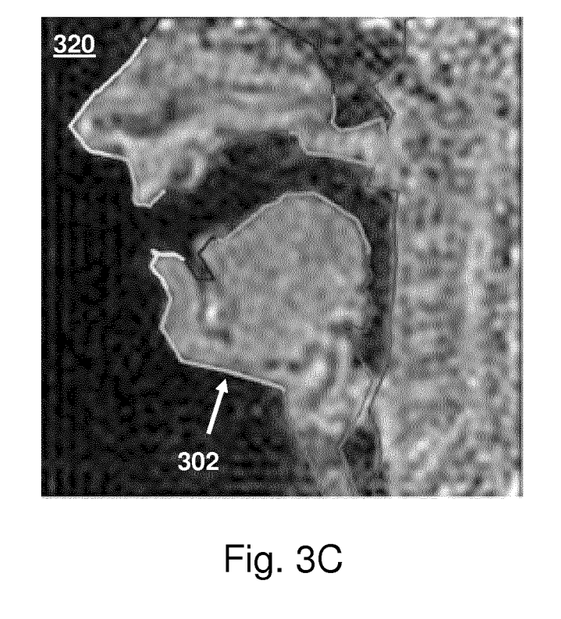
FIG. 3C shows the medical atlas having been registered to the medical image in accordance with a model learned by Reinforcement Learning.

FIG. 3C shows the medical atlas having been registered to the medical image in accordance with a model learned by Reinforcement Learning. The quality of match may be similar to that obtained by the registration technique described in the paper "*Region segmentation in the frequency domain applied to upper airway real-time magnetic resonance images*" by Erik Bresch et al., Medical Imaging, IEEE Transactions on 28.3 (2009): 323-338. However, the solution proposed in the above paper is designed only for this particular atlas, with heuristic components that are only empirically justified. The Reinforcement Learning allows a model to be learned for different atlas matching problems, e.g., different anatomical structures, different body parts, different types of atlases, different imaging modalities, etc.

Namely, the atlas registration problem has been cast by the inventors in the Reinforcement Learning framework, in that a principled approach is applied to learn the optimal sequence of transformation actions by exploration. However, the inventors have recognized that there may be two significant challenges to casting the atlas registration as a Reinforcement Learning problem. Namely, the input to the RL algorithm is the medical image and the medical atlas, the latter being typically a geometric description and/or template image. Using this input as a state for the RL algorithm poses the first challenge, in that the high dimensionality of the image data and atlas data is unsuitable to be used directly as a state for RL. Accordingly, a set of features is extracted from the atlas data and the image data. The set of features may be manually defined. Alternatively, the set of features to be extracted may be learned using a machine learning algorithm. In particular, a Deep Convolutional Neural Network model may be used to generate a high-level state space representation using the image data and the atlas data as an input. This high-level state space typically has a manageable size and will allow for efficient Reinforcement Learning.

Another challenge of casting the atlas registration as a Reinforcement Learning problem is that typically all possible transformations to the atlas need to be defined as actions in the RL framework. However, there are typically a large number of available transformations, which makes the action space also large. To address this problem, the transformation actions may be hierarchically structured. Hierarchical structuring of the transformations to the atlas is a known approach in the domain of atlas registration that allow for efficient heuristics design, e.g., as described in the aforementioned paper by Erik Bresch et al. This approach may be applied within the RL framework, thereby making the set of available transformation actions at any point in time manageable for the RL framework.

The hierarchical structuring as described in section IV.C "*Hierarchical Gradient Descent Procedure*" of the aforementioned paper by Erik Bresch et al. is hereby incorporated by reference as an example of how the action space may be hierarchically structured. Namely, the described model of the human vocal tract may be optimized by transformation actions which are hierarchically structured into four levels:

Level 1: Allowing only, as transformation actions, translation and rotation of the entire 3-region model geometry, thereby compensating for the subject's in-plane head motion.

Level 2: Allowing only, as transformation actions, translation and rotation of each region's boundary, thereby fitting the model to the rough current vocal tract posture.

Level 3: Allowing only, as transformation actions, rigid transformations, e.g., translation, rotation, and scaling, of each anatomical section obeying the section-specific boosting factors of Table III-Table V of the aforementioned paper.

Level 4: Allowing, as transformation actions, independent movement of all individual vertices of all regions.

Thus, this approach tries to find a good global match first and then zooms into optimizing smaller details. The RL algorithm may thus be constrained in its actions in that actions of a higher level can only be followed by actions of a lower level, and not vice versa. It will be appreciated that the above is a non-limiting example, and that alternative ways of hierarchically structuring the action space, e.g., for different types of medical images, different types of medical atlases, etc., are within reach of the skilled person.

With further reference to the proposed application of Reinforcement Learning to medical atlas registration, the following is noted. A general system model may comprise an agent which may execute actions on the environment while it may receive information about the current state of the environment as well as its current reward. The agent's task may be to choose actions that maximize the reward in the future even if that means to temporarily choose suboptimal actions. However, what is a good policy for the agent to follow, and how would that policy be implemented? Bresch & Narayanan have previously implemented fixed-schedule policy that was human-designed using trial and error. A more principled and adaptive approach comes from the theory of Reinforcement Learning. The core of the system is the Reinforcement Learning Agent (RLA) which is commonly implemented as a state machine. Generally speaking, the agent may solve a Markov Decision Process (MDP) by finding an optimal sequence of steps that will take the system to a desired state.

In an advantageous embodiment of the invention as claimed, the RLA may be enabled to execute actions which deform the medical atlas, and to make decisions (e.g., by solving the Bellman equation) on how to transform the medical atlas based on the current reward information and based on "Q" information which may be generated by a Deep Neural Network from sensory input: Q=f (input image, atlas, action). The Q-information may allow the RLA to compute an estimate of the expected reward (in the future) for any possible action, and so the RLA may best possibly exploit the available transformation possibilities and make a good action choice. Additionally, the RLA may explore the reward-outcome of actions and retain this learned information in the Deep Neural Network. For this, the RLA may also manage the updates of the Deep Neural Network. Initially, the Deep Neural Network may be randomly initialized or it may already be pre-trained from previous image registrations. As such, the domain specific elements in this system may be:

the reward function, being, e.g., the energy of the difference image between medical image and thus-far registered medical atlas, and the atlas, its parametrization, and its specific transformation action set.

Figure 4:
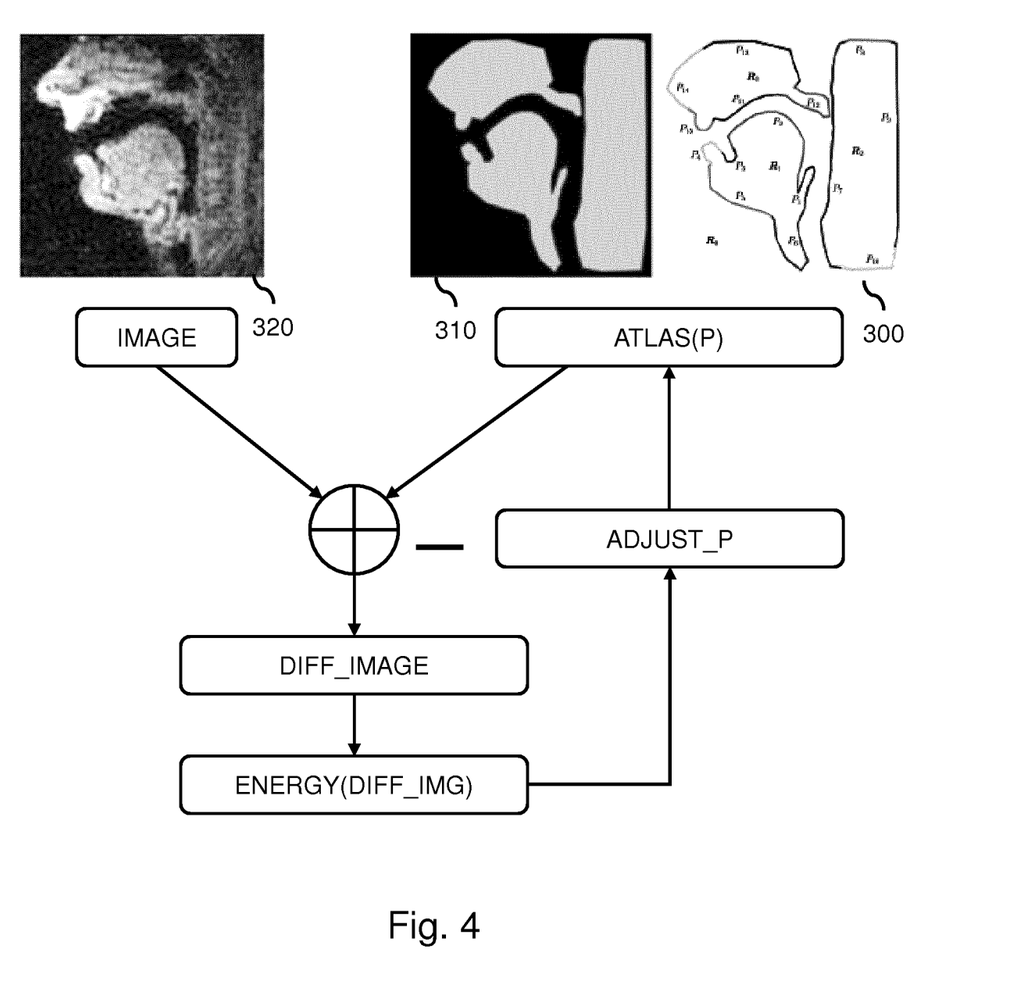
FIG. 4 illustrates a process of optimizing the registration of the medical atlas.
Figure 5:
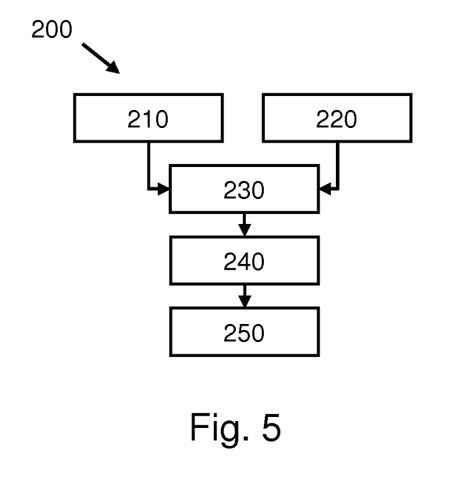
FIG. 5 shows a method of enabling atlas registration in medical imaging.

FIG. 4 illustrates a process of optimizing the registration of the medical atlas. Here, the medical image 320 (labeled "IMAGE" in FIG. 4) and the medical atlas 300 and accompanying image model 310 are used as input. In particular, the medical atlas 300 and accompanying image model 310 are used in as far as they have been transformed by a parameter set P of the model (labeled "ATLAS(P)"), which may represent the thus-far applied transformation actions. A difference may be determined between the medical image 320 and the image model 310, yielding a difference image (labeled "DIFF_IMAGE"). The energy of the difference image may then be determined by an energy function (labeled "ENERGY(DIFF_IMG")), which may represent a quantification of the degree of mismatch between the medical image 320 and the thus-far registered image model 310. Effectively, the minimization of the energy of the difference image may represent a reward. The Reinforcement Learning may use a suitably configured reward function, e.g., one which rewards the minimization of the energy of the difference image. The parameter set P of the model may then be adjusted by the RL algorithm (labeled "ADJUST_P"). The above described process may be repeated until the energy of the difference image is minimized. FIG. 5 shows a method 200 for enabling atlas registration in medical imaging. It is noted that the method 200 may, but does not need to, correspond to an operation of the system 100 as described with reference to FIG. 1.

The method 200 may comprise, in an operation titled "ACCESSING ATLAS DATA", accessing 210 atlas data defining the medical atlas. The method 200 may further comprise, in an operation titled "ACCESSING IMAGE DATA", accessing 220 image data of the medical image. The method 200 may further comprise, in an operation titled "DETERMINING STATE SPACE", determining 230 a state space for a Reinforcement Learning algorithm on the basis of a set of features extracted from i) the atlas data and ii) the image data. The method 200 may further comprise, in an operation titled "DETERMINING ACTION SPACE", determining 240 an action space for the Reinforcement Learning algorithm on the basis of a set of transformation actions available to be applied to the medical atlas. The method 200 may further comprise, in an operation titled "EXECUTING RL ALGORITHM", executing 250 the Reinforcement Learning algorithm to learn a model for matching the medical atlas to the medical image, wherein said learning is on the basis of a reward function quantifying a degree of match between the medical atlas and the medical image. It will be appreciated that the above operation may be performed in any suitable order, e.g., consecutively, simultaneously, or a combination thereof, subject to, where applicable, a particular order being necessitated, e.g., by input/output relations.

Figure 6:
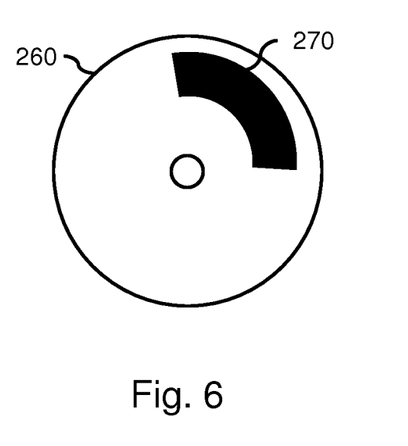
FIG. 6 shows a computer readable medium comprising instructions for causing a processor system to perform the method.

The method 200 may be implemented on a computer as a computer implemented method, as dedicated hardware, or as a combination of both. As also illustrated in FIG. 6, instructions for the computer, e.g., executable code, may be stored on a computer readable medium 260, e.g., in the form of a series 270 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 260.

It will be appreciated that, in accordance with the abstract of the present application, a system and method may be provided for enabling atlas registration in medical imaging, said atlas registration comprising matching a medical atlas to a medical image. The system and method may execute a Reinforcement Learning (RL) algorithm to learn a model for matching the medical atlas to the medical image, wherein said learning is on the basis of a reward function quantifying a degree of match between the medical atlas and the medical image. The state space of the RL algorithm may be determined on the basis of a set of features extracted from i) the atlas data and ii) the image data. Moreover, the action space for the RL algorithm may be determined on the basis of a set of transformation actions available to be applied to the medical atlas. As such, a model may be obtained for atlas registration in medical imaging without the use, or with a reduced use, of heuristics. By using a machine learning based approach, the solution can easily be applied to different atlas matching problems, e.g., to different types of medical atlases and/or medical images.

It will be appreciated that matching a medical atlas to a medical image is to be understood as also including matching the medical image to the medical atlas.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling atlas registration in medical imaging, said atlas registration comprising matching a medical atlas to a medical image, the system comprising:

a first input interface for accessing atlas data defining the medical atlas;

a second input interface for accessing image data of the medical image;

a processor configured to:
- execute a Reinforcement Learning algorithm to learn a model for matching the medical atlas to the medical image, wherein said learning is on a basis of a reward function quantifying a degree of match between the medical atlas and the medical image;
- determine a state space for the Reinforcement Learning algorithm on a basis of a set of features extracted from i) the atlas data and ii) the image data;
- apply a Convolutional Neural Network or Autoencoder to the atlas data and the image data to determine the set of features; and
- determine an action space for the Reinforcement Learning algorithm on a basis of a predefined set of transformation actions which are available to be applied to the medical atlas, wherein the action space is structured into different levels;

wherein each of the different levels comprises a subset of the transformation actions, and wherein the different levels form a hierarchy of transformation actions in which selection of a sequence of transformation actions by the Reinforcement Learning algorithm is restricted to a downward progression in the hierarchy.

2. The system according to claim 1, wherein the processor is configured to learn the set of features to be extracted from the atlas data and the image data using a machine learning algorithm.

3. The system according to claim 1, wherein the action space is hierarchically structured to comprise less restrictive transformation actions upwards in the hierarchy and more restrictive transformation actions downwards in said hierarchy.

4. The system according to claim 3, wherein the processor is configured to perform said hierarchically structuring of the action space using a machine learning algorithm or using pre-determined heuristics.

5. The system according to claim 3 wherein the processor is configured to determine the state space for the Reinforcement Learning algorithm further based on a current level in the hierarchy of transformation actions.

6. The system according to claim 1, wherein the predefined set of transformation actions, which is available to be applied to the medical atlas, is defined by the atlas data.

7. The system according to claim 1, wherein the processor is configured to determine the state space for the Reinforcement Learning algorithm further based on landmark data defining landmarks in the medical atlas.

8. The system according to claim 1, wherein the Reinforcement Learning algorithm is a Deep Reinforcement Learning algorithm.

9. A workstation comprising the system according to claim 1.

10. A non-transitory computer readable medium comprising data representing a model for atlas registration in medical imaging as generated by the system according to claim 1.

11. A method of enabling atlas registration in medical imaging, said atlas registration comprising matching a medical atlas to a medical image, comprising:
- accessing atlas data defining the medical atlas;
- accessing image data of the medical image;
- executing a Reinforcement Learning algorithm to learn a model for matching the medical atlas to the medical image, wherein said learning is on a basis of a reward function quantifying a degree of match between the medical atlas and the medical image;
- determining a state space for the Reinforcement Learning algorithm on a basis of a set of features extracted from i) the atlas data and ii) the image data;
- applying a Convolutional Neural Network or Autoencoder to the atlas data and the image data to determine the set of features; and
- determining an action space for the Reinforcement Learning algorithm on a basis of a predefined set of transformation actions which are available to be applied to the medical atlas, wherein the action space is structured into different levels;
- wherein each of the different levels comprises a subset of the transformation actions, and wherein the different levels form a hierarchy of transformation actions in which selection of a sequence of transformation actions by the Reinforcement Learning algorithm is restricted to a downward progression in the hierarchy.

12. A non-transitory computer readable medium comprising data representing instructions to cause a processor system to perform the method according to claim 11.

* * * * *